US012478783B2

(12) United States Patent
Tass

(10) Patent No.: US 12,478,783 B2
(45) Date of Patent: Nov. 25, 2025

(54) MEDICAL TREATMENT DEVICE AND METHOD FOR STIMULATING NEURONS OF A PATIENT TO SUPPRESS A PATHOLOGICALLY SYNCHRONOUS ACTIVITY THEREOF

(71) Applicant: GRETAP AG, Zug (CH)

(72) Inventor: Peter Alexander Tass, Tegernsee (DE)

(73) Assignee: GRETAP AG, Zug (CH)

( * ) Notice: Subject to any disclaimer, the term of this patent is extended or adjusted under 35 U.S.C. 154(b) by 1100 days.

(21) Appl. No.: 17/255,385

(22) PCT Filed: Jun. 24, 2019

(86) PCT No.: PCT/EP2019/066671
§ 371 (c)(1),
(2) Date: Dec. 22, 2020

(87) PCT Pub. No.: WO2019/243634
PCT Pub. Date: Dec. 26, 2019

(65) Prior Publication Data

US 2021/0260375 A1 Aug. 26, 2021

Related U.S. Application Data

(60) Provisional application No. 62/688,489, filed on Jun. 22, 2018.

(51) Int. Cl.
*A61N 1/36* (2006.01)
*A61N 1/04* (2006.01)

(52) U.S. Cl.
CPC ....... *A61N 1/36025* (2013.01); *A61N 1/0456* (2013.01); *A61N 1/36031* (2017.08); *A61N 1/36034* (2017.08)

(58) Field of Classification Search
CPC .............. A61N 1/36025; A61N 1/0456; A61N 1/36031
See application file for complete search history.

(56) References Cited

U.S. PATENT DOCUMENTS 9,014,824 B2 4/2015 Kroll-Orywahl et al.
2006/0212089 A1* 9/2006 Tass .................. A61N 1/36135 607/45

(Continued)

FOREIGN PATENT DOCUMENTS

CA 3011993 A1 8/2017
CN 102905760 A 1/2013

(Continued)

OTHER PUBLICATIONS

International Search Report and Written Opinion for Application No. PCT/EP2019/066671, dated Aug. 5, 2019, 12 pages.

(Continued)

*Primary Examiner* — James M Kish
*Assistant Examiner* — James Moss
(74) *Attorney, Agent, or Firm* — McCarter & English, LLP

(57) ABSTRACT

The present invention pertains to a medical treatment device for stimulating neurons of a patient to suppress a pathologically synchronous activity, the device comprises at least three non-invasive stimulating units for generating stimuli to a patient's body, and a control unit for selectively and intermittently actuating the stimulating units in a sequence of actuating periods. The control unit is configured to, across the sequence of actuating periods, variedly determine for each actuating period a number n of stimulating units to be simultaneously actuated during the respective actuating period.

20 Claims, 10 Drawing Sheets

(56) References Cited

U.S. PATENT DOCUMENTS

| | | | | |
|---|---|---|---|---|
| 2010/0331912 | A1 | 12/2010 | Tass et al. | |
| 2013/0041296 | A1* | 2/2013 | Tass | A61H 23/0245 601/46 |
| 2013/0090519 | A1* | 4/2013 | Tass | A61H 23/00 600/27 |
| 2014/0364923 | A1* | 12/2014 | Legay | A61N 1/36053 607/73 |
| 2021/0205619 | A1* | 7/2021 | Wong | A61N 1/36031 |

FOREIGN PATENT DOCUMENTS

| | | | |
|---|---|---|---|
| CN | 103492023 | A | 1/2014 |
| CN | 104144729 | A | 11/2014 |
| CN | 106413805 | A | 2/2017 |
| CN | 107174735 | A | 9/2017 |
| CN | 107405487 | A | 11/2017 |
| GB | 2548148 | A | 9/2017 |
| JP | 2012-505674 | A | 3/2012 |
| JP | 2013-519400 | A | 5/2013 |
| JP | 2015-507957 | A | 3/2015 |
| JP | 2017-535364 | A | 11/2017 |
| JP | 2018-505735 | A | 3/2018 |
| WO | WO-2015/187712 | A1 | 12/2015 |
| WO | 2017/114878 | A1 | 7/2017 |
| WO | 2017/132067 | A2 | 8/2017 |
| WO | WO-2019/243634 | A1 | 12/2019 |

OTHER PUBLICATIONS

Japanese Office Action for Application No. 2020-571598, dated Mar. 8, 2022, 20 pages.

* cited by examiner

MEDICAL TREATMENT DEVICE AND METHOD FOR STIMULATING NEURONS OF A PATIENT TO SUPPRESS A PATHOLOGICALLY SYNCHRONOUS ACTIVITY THEREOF

CROSS-REFERENCE TO RELATED APPLICATIONS

This application is a 35 U.S.C. § 371 national stage filing of International Application No. PCT/EP2019/066671, filed on Jun. 24, 2019, which claims priority to U.S. Provisional Application No. 62/688,489, filed on Jun. 22, 2018. The entire contents of each of the aforementioned applications are incorporated herein by reference.

TECHNICAL FIELD

The invention relates to a medical treatment device and a respective method for stimulating neurons of a patient to suppress a pathologically synchronous activity of the neurons.

TECHNOLOGICAL BACKGROUND

Several brain disorders, such as Parkinson's disease, are characterized by abnormally strong synchronous activity of neurons, i.e. strongly synchronized neuronal firing or bursting. Besides Parkinson's disease, this may also apply, for example, to essential tremor, dystonia, dysfunction after stroke, epilepsy, depression, migraine, tension headache, obsessive-compulsive disorder, irritable bowel syndrome, chronic pain syndromes, pelvic pain, dissociation in borderline personality disorder and post-traumatic stress disorder.

The pharmacological treatment for Parkinson's disease with, for example, L-DOPA may have limited therapeutic effects and it may cause significant long-term side effects. High-frequency Deep Brain Stimulation (DBS) for Parkinson's disease is a standard for medically refractory patients in advanced stages of Parkinson's disease. However, DBS requires surgical procedures associated with a significant risk. For instance, depth electrode implantation in dedicated target areas in the brain may cause bleedings. Furthermore, standard continuous high-frequency DBS may cause side effects.

Further, a non-invasive, vibrotactile multichannel stimulation treatment is known to counteract Parkinsonian signs. The disadvantage of this non-invasive approach lies within an inherently periodic structure of employed stimulations. As to substance, if particular stimulation parameters, such as the repetition rate of sequences of stimuli, are not properly tuned to the dominant frequency of the abnormally active neurons, the stimulation may be ineffective. In particular, in a non-invasive setup, it is difficult to obtain reliable estimates of frequency characteristics of abnormal brain activity due to limitations of chronic non-invasive electroencephalography (EEG) recordings. More importantly, several brain disorders are characterized by abnormal brain rhythms of different frequencies, e.g., around 4 Hz to 5 Hz related to Parkinson's tremor, as opposed to 9 Hz to 35 Hz related to bradykinesia and rigor in Parkinson's disease. Furthermore, multiple central oscillators (i.e. brain rhythms) cause the tremor in different extremities of patients with Parkinson's disease. Without feedback signals from chronically implanted brain electrodes it may be, hence, difficult to achieve optimal stimulation results with the stimulation patterns used so far.

It has been found that abnormally upregulated synaptic connections may lead to abnormal synchronous activity of neurons. However, repeated coincident activation of neurons may lead to an increase of the strength of their mutual synaptic connections. Thus, in case the stimulations generated in the known non-invasive, vibrotactile multichannel stimulation treatment repeatedly and coincidently overlap with the pathologically synchronous activity of the neurons, the treatment may even cause an unintentional strengthening of the pathologically synchronous activity of the neurons.

SUMMARY OF THE INVENTION

In view of the technical background, it is an object of the present invention to suggest an improved non-invasive medical treatment device and a respective method enabling to robustly and effectively suppress pathologically synchronous activities of neurons, i.e. in a patient's brain.

The object is solved by means of a medical treatment device with the features of claim 1. Preferred embodiments can be taken from the Figures, the specification as well as the dependent claims.

Accordingly, in a first aspect, a medical treatment device for stimulating neurons of a patient to suppress a pathologically synchronous activity is proposed, which comprises at least three noninvasive stimulating units for generating stimuli to a patient's body. The medical treatment device further comprises a control unit for selectively and intermittently actuating the stimulating units in a sequence of actuating periods, wherein the control unit, across the sequence of actuating periods, is configured to variedly determine for each actuating period a number n of stimulating units to be simultaneously actuated during the respective actuating period.

According to further aspects, a medical treatment glove, a medical treatment band, a medical treatment seat pad and a medical treatment sole for stimulating neurons of a patient to suppress a pathologically synchronous activity are proposed, each of which comprises at least three noninvasive stimulating units for generating stimuli to a patient's body and a control unit for selectively and intermittently actuating the stimulating units in a sequence of actuating periods, wherein the control unit, across the sequence of actuating periods, is configured to variedly determine for each actuating period a number n of stimulating units to be simultaneously actuated during the respective actuating period.

According to a further aspect, a medical treatment system for stimulating neurons of a patient to suppress a pathologically synchronous activity is proposed, the medical treatment system comprising two or more medical treatment devices.

According to a further aspect, a medical treatment method for stimulating neurons of a patient to suppress a pathologically synchronous activity is proposed. The method comprises the steps of providing at least three non-invasive stimulating units for generating stimuli to a patient's body, and of selectively and intermittently actuating the stimulating units according to a sequence of actuating periods, wherein a number n of stimulating units to be simultaneously actuated during the respective actuating period variedly varies across the sequence, and wherein, during at least one of the actuating periods, three stimulating units are simultaneously actuated.

BRIEF DESCRIPTION OF THE DRAWINGS

The present disclosure will be more readily appreciated by reference to the following detailed description when being considered in connection with the accompanying drawings in which.

DETAILED DESCRIPTION

Figure 1:
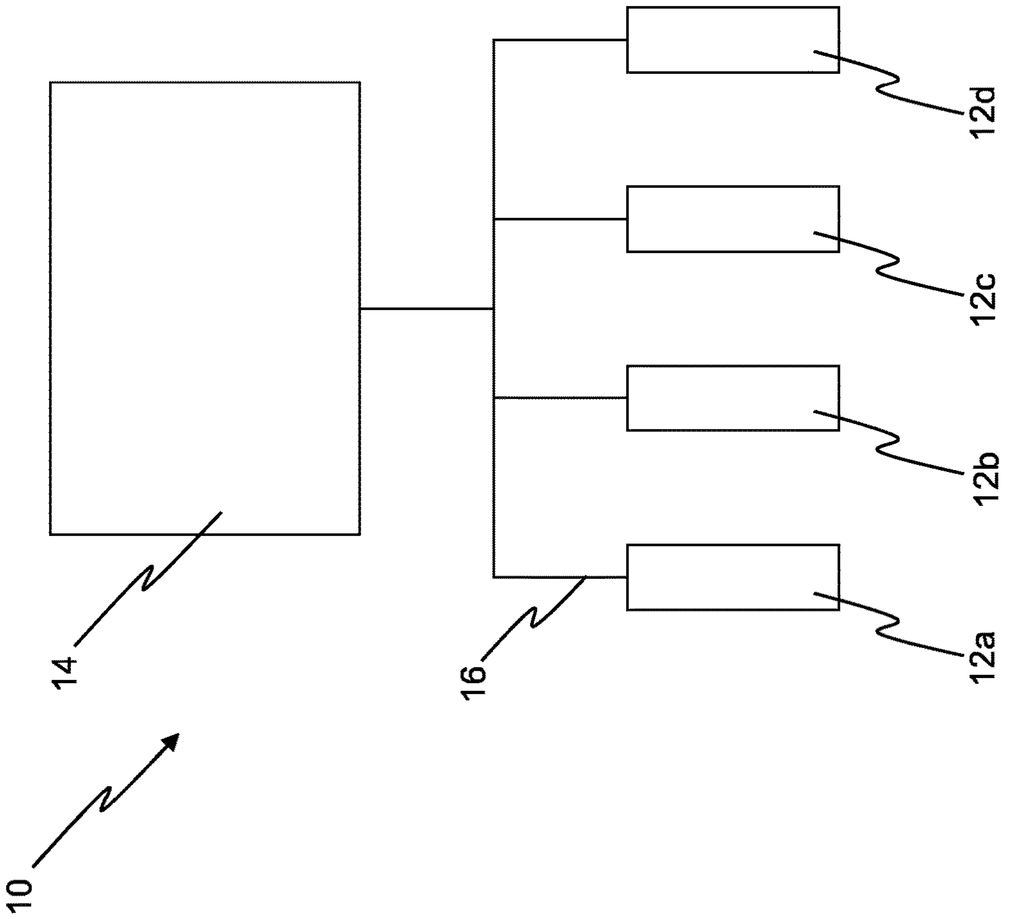
FIG. 1 is a schematic illustration of a medical treatment device for stimulating neurons of a patient to suppress a pathologically synchronous activity.

In the following, the invention will be explained in more detail with reference to the accompanying figures. In the Figures, like elements are denoted by identical reference numerals and repeated description thereof may be omitted in order to avoid redundancies.

FIG. 1 schematically shows a medical treatment device 10 for stimulating neurons of a patient to suppress a pathologically synchronous activity of the neurons.

The medical treatment device 10 is intended to be used for the treatment of neurological or psychiatric diseases, in particular, Parkinsons's disease, essential tremors, dystonia, etc. To that end, the medical treatment device 10 may also be used for the treatment of other neurological or psychiatric diseases, such as epilepsy, tremors as a result of Multiple Sclerosis as well as other pathological tremors, depression, movement disorders, diseases of the cerebellum, obsessive compulsive disorders, Tourette syndrome, functional disorders following a stroke, spastics, tinnitus, sleep disorders, schizophrenia, irritable colon syndrome, addictive disorders, personality disorders, attention deficit disorder, attention deficit hyperactivity syndrome, gaming addiction, neuroses, eating disorders, burnout syndrome, fibromyalgea, migraine, cluster head ache, general head-aches, neuronalgia, ataxy, tic disorder or hypertension, and also for the treatment of other diseases.

The aforementioned diseases can be caused by a disorder of the bioelectric communication of groups of neuronal cells which are connected to one another in specific circuits. Hereby, a neuron population generates a continuous pathological neuronal activity and a pathological connectivity (network structure) possibly associated therewith. In this respect, a large number of neurons form synchronous action potentials, this means that the concerned neurons fire or burst excessively synchronously. In addition, the pathological neuron population has an oscillating neuronal activity, this means that the neurons fire or burst rhythmically. In the case of neurological or psychiatric diseases, the mean frequency of the pathological rhythmic activity of the concerned groups of neurons approximately may be in the range of 1 Hz to 30 Hz, but may, however, also be outside of this range. By contrast, the neurons of healthy people fire or burst qualitatively differently, for example, in an uncorrelated manner.

In other words, each of the aforementioned diseases may be characterized by at least one neuronal population in the brain or spinal cord of the patient which has a pathological synchronous neuronal activity. For suppressing such a pathologically synchronous activity, the medical treatment device 10 is configured to stimulate the affected neuronal population so as to cause the affected neural population to fire or burst in an uncorrelated manner, i.e. non-synchronously.

Specifically, the medical treatment device 10 is a non-invasive treatment device. This means that the medical treatment device 10 deploys a non-invasive procedure to achieve the intended therapeutic effect. In other words, in an operational state, the medical treatment device 10 is not implanted into a patient's body, i.e. associated with an intervention procedure into the patient's body.

For acting on the patient's body, the medical treatment device 10 comprises four non-invasive stimulating units 12*a-d*, each of which is configured to generate stimuli to the patient's body. In other words, the stimulating units 12*a-d* are configured to induce stimuli to the patient's body when being in contact with a body surface of the patient. Accordingly, the stimulating units 12*a-d* are intended to being fastened to the patient. For that reason, the medical treatment device 10 further comprises fastening means (not shown) for releasably fastening the stimulating units 12*a-d* to the patient's body. Specifically, the fastening means are provided such that the stimulating units 12*a-d* are fastened to different sites of the patient's body. Thus, in a state of the medical treatment device 10 fastened to the patient's body, the stimulating units 12*a-d* are spaced apart from one another. In this way, the stimulating units 12*a-d* are configured to generate stimuli to different sites of the patient's body.

Although the shown embodiment comprises four stimulating units 12*a-d*, satisfying therapeutic effects may also be achieved with a medical treatment device having three stimulating units. Thus, in another embodiment, the medical treatment device may have three or more than four stimulating units.

Stimuli generated by the stimulating units 12*a-d*, in general, refer to excitations capable of being sensed by the patient's body, i.e. by respective receptors. Such stimuli may have the modality of, for example, optical stimuli, acoustic stimuli, tactile stimuli, vibratory stimuli, electrical stimuli and/or thermal stimuli. These stimuli may be sensed by receptors, for example, in the eyes, the ears and/or the skin of the patient depending of the stimuli's modality and are guided from there to a patient's nerve system causing an actuation of neurons in the patient's brain or spinal cord.

Thus, for suppressing the neuronal population affected by the pathologically synchronous activity, the stimulating units 12*a-d* are configured to generate stimuli to the patient's body which, upon being sensed by receptors of the patient's body and guided to its nerve system, at least partially cause actuation of the affected neuronal population, i.e. in the patient's brain. For doing so, the modality and characteristic of the generated stimuli as well as the intended location, at which they are to be induced into the patient's body, are respectively set as described in the following in more detail.

Each stimulating unit 12*a-d* may be configured to generate at least one of the aforementioned modalities of stimuli. Across the plurality of stimulating units 12*a-d*, the stimulating units 12*a-d* may be configured to generate the same modality or different modalities of stimuli.

In the embodiment shown in FIG. 1, each of the stimulating units 12*a-d* is configured to generate vibratory and/or tactile stimuli. In such a configuration, the stimulating units 12*a-d* may comprise a stimulation element, such as a rod, configured to mechanically act upon the patient's skin. The stimulation element may be driven by an electro-mechanical actuator for converting electrical energy into a movement of the stimulation element. For example, the electro-mechanical actuator may be provided in the form of an equal current motor, a voice coil, a piezo-electric transducer or a transformer built up of electro-active polymers which change their shape on the application of an electric current. For providing electrical energy to the electro-mechanical actuator, the stimulating units 12*a-d* may comprise or be connected to an energy source, i.e. in the form of a battery. By such a configuration, the stimulating unit 12*a-d* may be variably driven so as to generate vibratory stimuli of different or varying vibration frequencies and vibration amplitudes. Accordingly, the stimulating units 12*a-d* can be operated in different operational modes, in which the respective stimulating units 12*a-d* generate different stimuli, i.e. in terms of stimuli duration, vibration frequency, vibration amplitude, etc.

In general, the human skin comprises mechanoreceptive afferent units capable of sensing stimuli, i.e. tactile or vibratory stimuli, which have been classified into two major categories, namely into fast adapting units (FA) and slowly adapting units (SA). The FA units respond to moving stimuli as well as the onset and removal of a step stimulus. In contrast, the SA units respond with a sustained discharge. In addition, based on the properties of their receptive fields, both categories are further classified into two different types. The fast-adapting type I (FA I) units, also referred to as RA (rapidly adapting) units, and the slow-adapting type I (SA I) units form a small, but clearly delimited receptive fields on the surface of the skin. In contrast, the receptive fields formed by the fast-adapting type II (FA II) units, also referred to as PC (Pacinian corpuscles) units, and the slow-adapting type II (SA II) are wider and have obscure borders.

Typically, the distribution and density of the different types of mechanoreceptors differs in dependence on the position on the human skin. For example, regarding the glabrous skin of the human hand, the density of FA I units is relatively high in an area of the fingertips. By contrast, the density of FA II units is relatively high in an area at the back of the fingers and the hand.

The four different types of human cutaneous mechanoreceptors respond optimally to qualitatively different stimuli. Specifically, edge stimuli and stretch stimuli are optimal for SA I and SA II mechanoreceptors, respectively. SA I units often have a rather irregular sustained discharge, whereas SA II units discharge in a regular manner, but often display spontaneous discharge in the absence of tactile stimulation. Vibratory perpendicular sinusoidal skin displacements in the range between about 30 Hz to about 60 Hz are optimal stimuli for FA I units, whereas vibratory stimuli in the range between about 100 Hz to about 300 Hz are optimal stimuli for FA II units. FA I and, especially, SA I units have a pronounced edge contour sensitivity and, hence, their response is stronger when a stimulating contactor surface which is not completely contained in the receptive field. Accordingly, to enhance the FA I responses, instead of a flat, spatially homogenous contactor surface of the stimulation element one could use a contactor surface with a spatially inhomogeneous indentation profile.

In the shown embodiment, the stimulating units 12*a-d* may be designed and configured to generate stimuli adapted to the response characteristic of FA I, FA II, SA I and/or SA II units. In this configuration, each of the stimulating units 12*a-d* may be configured to generate stimuli adapted to response to at least one of the FA I, FA II, SA I and SA II units. For example, the medical treatment device 10 may comprise stimulating units 12*a-d* which are configured to generate stimuli which target merely one of the FA I, FA II, SA I and SA II units. In other words, these stimulating units 12*ad* generate stimuli which are adapted to the response characteristic of one of the FA I, FA II, SA I and SA II units. Alternatively or additionally, the medical treatment device 10 may comprise stimulating units 12*a-d* which are configured to generate stimuli targeting more than one of the FA I, FA II, SA I and SA II units. For example, such a stimulating unit 12*a-d* may be configured to generate stimuli which are sensed by more than one of the FA I, FA II, SA I and SA II units. Alternatively or additionally, such a stimulating unit 12*a-d* may be configured to being operated in different operational modes, in which different stimuli are generated which, respectively, are adapted to a response characteristic of different FA I, FA II, SA I and SA II units.

Specifically, for targeting FA I type receptors, a stimulating unit 12*a-d* may be configured to generate vibratory stimuli with a vibration frequency between 30 Hz to 60 Hz, i.e. 30 Hz, and a vibration peak-to-peak amplitude of 0.25 mm. For example, this stimulating unit 12*a-d* may be intended to being fastened to a fingertip of the patient. Further, for targeting FA II type receptors, a stimulating unit 12*a-d* may be configured to generate vibratory stimuli with a vibratory frequency between 100 Hz to 300 Hz, i.e. 250 Hz, and a peak-to-peak amplitude of 2.0 mm. For example, this stimulating unit 12*a-d* may be intended to being fastened to a back of a finger or hand of the patient. Further, it has been found that for sufficiently large vibration peak-to-peak amplitudes, the low-frequency vibration targeting FA I type receptors will additionally activate FA II type receptors and vice versa. Thus, by increasing the peak-to-peak amplitude, e.g. to a peak-to-peak amplitude of 3.0 mm, each of the above mentioned stimulating units 12*a-d* may generate vibratory stimuli adapted to stimulate both FA I and FA II type receptors.

The medical treatment device 10 further comprises a control unit 14 for selectively and intermittently actuating the stimulating units 12*a-d*. The control unit 14 is connected to each one of the stimulating units 12*a-d* via a connecting wire 16, through which control signals are guided from the control unit 14 to the stimulating units 12*a-d* for actuating the same.

Figure 2:
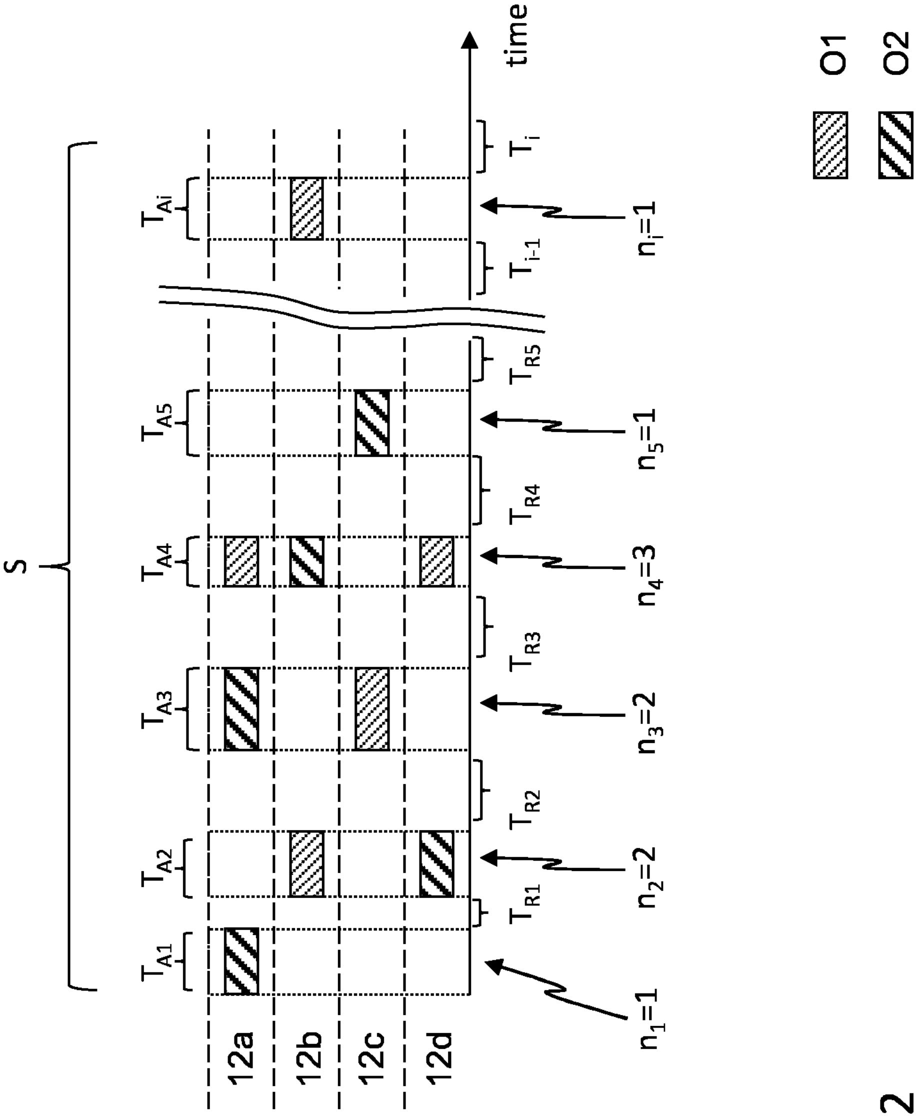
FIG. 2 schematically shows a sequence of actuating periods, according to which non-invasive stimulating units of the medical treatment device are actuated to suppress the pathologically synchronous activity of patient's neurons.

Specifically, the control unit 14 is configured for actuating the stimulating units 12*a-d* in a sequence S of successive actuating periods $T_{A1, \ldots, Ai}$, wherein character "i" refers to a total number of actuating periods within the sequence S. FIG. 2 shows the sequence S of successive actuating periods $T_{A1, \ldots, Ai}$, according to which the stimulating units 12*a-d* of the medical treatment device 10 are actuated to suppress the pathologically synchronous activity of patient's neurons. The sequence S is generated by the control unit 14 and forms a control sequence or control pattern illustrating the actuation of stimulating units 12*a-d* over the course of time. Thus, the sequence S illustrates a time period in which the stimulating units 12*a-d* of the medical treatment device 10 are selectively and intermittently actuated. The sequence S of actuating periods $T_{A1, \ldots, Ai}$ may have a duration corresponding to a duration of a treatment procedure, e.g. a daily treatment procedure, performed by the medical treatment device 10. For example, the sequence S may have a duration of 120 Minutes.

The sequence S comprises a number i of time shifted, non-overlapping actuating periods $T_{A1, \ldots, Ai}$. In this context, the term "actuating period" refers to a time period within the sequence S, during which at least one of the stimulating units 12*a-d* is actuated so as to generate stimuli to the patient's body. The duration of the actuating periods $T_{A1, \ldots, Ai}$ thus corresponds to a length of a single stimuli generated by the stimulating units 12*a-d*. For example, the actuating periods $T_{A1, \ldots, Ai}$ may have a duration between 25 ms to 3 s, i.e. about 125 ms. In an alternative embodiment, the actuating periods within the sequence may at least partially overlap.

As depicted in FIG. 2, between successive actuating periods $T_{A1, \ldots, Ai}$, resting periods $T_{R1, \ldots, Ri}$ are scheduled. The term "resting period" refers to a time period within the sequence S during which none of the stimulating units 12*a-d* is actuated. Accordingly, during the resting periods $T_{R1, \ldots, Ri}$, the patient's body is not subjected to stimuli generated by the stimulating units 12*a-d* of the medical treatment device 10.

In FIG. 2, the actuation of the respective stimulating units 12*a-d* is illustrated by means of dashed fields positioned within the actuating periods $T_{A1, \ldots, Ai}$. During the actuating periods $T_{A1, \ldots, Ai}$ the control unit 14 may actuate exclusively a single stimulating unit 12, as depicted by the actuating periods $T_{A1}$, $T_{A5}$, and $T_{Ai}$ in FIG. 2. Alternatively, as depicted in FIG. 2 by actuating periods $T_{A2}$, $T_{A3}$, and $T_{A4}$, the control unit 14 may simultaneously actuate more than one, for example 2 or 3, stimulating units 12*a-d* during the actuating periods $T_{A1, \ldots, Ai}$. In the context of the present disclosure, the number of stimulating units 12*a-d* to be simultaneously actuated during the respective actuating periods $T_{A1, \ldots, Ai}$ is denoted as "$n_{1 \ldots i}$", wherein n is an integer greater than 1. If n equals 1, this means that during the respective actuating period $T_{A1, \ldots, Ai}$ a single stimulating unit 12*a-d* is actuated individually. In contrast, if n is greater than 1, this means that during the respective actuating period $T_{A1, \ldots, Ai}$ more than one, i.e. n, stimulating units 12*a-d* are actuated simultaneously. In the sequence S depicted in FIG. 2, $n_1$, $n_5$ and $n_i$ equal 1; $n_2$ and $n_3$ equal 2; and $n_4$ equals 3.

More specifically, the control unit 14, across the sequence S of actuating periods $T_{A1, \ldots, Ai}$, is configured to variedly determine for each actuating period $T_{A1, \ldots, Ai}$ the number $n_{1, \ldots, i}$ of stimulating units 12*a-d* to be actuated during the respective actuating period. In this context, the term "variedly" means that the values for the number $n_{1, \ldots, i}$ diversely, i.e. non-periodically, varies across the sequence S.

Again, in this configuration, the control unit 14 may determine for the number $n_{1 \ldots i}$ a value of 1, meaning that merely a single stimulating unit 12*a-d* is to be actuated during the respective actuating period $T_{A1, \ldots, Ai}$. By contrast, if the control unit 14 determines for the number $n_{1, \ldots, i}$ a value greater than 1, this means that more than one stimulating units 12*a-d* are actuated simultaneously during that actuating period $T_{A1, \ldots, Ai}$.

Specifically, in order to increase variability of stimulus-induced neuronal activations, the control unit 14, for at least one of the actuating periods $T_{A1, \ldots, Ai}$, is configured to determine at least three stimulating units 12*a-d* to be simultaneously actuated, as depicted in FIG. 2 by actuating period $T_{A4}$. In other words, the control unit 14 is configured to determine for at least one of $n_{1, \ldots, i}$ a value that is equal to or greater than 3.

In the shown embodiment, the control unit 14 may determine for the number $n_{1, \ldots, i}$ a value between 1 and a preset maximum number of stimulating units to be actuated simultaneously. Accordingly, the number $n_{1, \ldots, i}$ is a integer between 1 and the maximum number of stimulating units to be actuated simultaneously. The maximum number may correspond to the total number of stimulating units 12*a-d* comprised in the medical treatment device 10. It has been found that, in case the medical treatment device 10 comprises more than three stimulating units, it may be less favorable to actuate all stimulating units simultaneously. Thus, the maximum number of stimulating units to be actuated simultaneously may correspond to a number which is smaller, i.e. smaller by 1, than the total number of stimulating units 12*a-d* comprised in the medical treatment device 10.

For variedly determining the numbers $n_{1, \ldots, i}$ across the sequence S, the control unit 14, for each of the actuating periods $T_{A1, \ldots, Ai}$, is configured to stochastically and/or deterministically and/or combined stochastically-deterministically determine the number $n_{1, \ldots, i}$ of stimulation units 12*a-d*. For example, for doing so, the control unit 14 may employ an exponential distribution process and/or a Markov process and/or any other suitable stochastic or deterministic or combined stochastic-deterministic process. In this way, regularities or periodicities in the sequence S may be avoided, thereby contributing to a robust and effective suppression of pathologically synchronous activity of the patient's neurons.

In a further development, the process of determining the number $n_{1, \ldots, i}$ of stimulation units may be performed such that values for the number $n_{1, \ldots, i}$ are provided with an equal probability or with differing probabilities. In this way, the frequency of occurrence for the individual values for the numbers $n_{1, \ldots, i}$ may be set across the sequence S. For example, in the shown sequence, the value 1 for the numbers $n_{1, \ldots, i}$ may be provided with a probability of 50%, the value 2 may be provided with a probability of 33%, and the value 3 may be provided with a probability of 16%. As a result, in the sequence S having i=6 actuating periods, the value 1 for $n_{1, \ldots, i}$ may be determined for three actuating periods, the value 2 for $n_{1, \ldots, i}$ may be determined for two actuating periods, and the value 3 for $n_{1, \ldots, i}$ may be determined for one actuating period.

Further, the control unit 14 is configured to, across the sequence S of actuating periods $T_{A1, \ldots, Ai}$, variedly select the determined number $n_{1, \ldots, i}$ of different stimulating units from a set of stimulating units comprising the at least three stimulating units 12*a-d*, wherein the selected stimulating units 12*a-d* are to be individually or simultaneously actuated during the respective actuating period $T_{A1, \ldots, Ai}$. In this context, the term "variedly" means that the selected stimulating units diversely, i.e. non-periodically, vary across the sequence S.

For example, in case the control unit 14 has determined for a specific actuating period $T_{A1, \ldots, Ai}$ that the respective number $n_{1, \ldots, i}$ equals 1, then the control unit 14 selects a single stimulating unit from the set of four stimulating units 12*a-d* that is to be actuated individually during the respective actuating period $T_{A1, \ldots, Ai}$. By contrast, in case the control unit 14 has determined for a specific actuating period $T_{A1, \ldots, Ai}$ that the respective number $n_{1, \ldots, i}$ equals 2, then the control unit 14 selects two different stimulating units from the set of four stimulating units 12*a-d* that are to be actuated simultaneously during the respective actuating period $T_{A1, \ldots, Ai}$.

For further increasing the variability of stimulus-induced neuronal activations, the control unit 14 is further configured to set for at least a first and a second actuating period, e.g. $T_{A1}$ and $T_{A5}$, the numbers $n_1$, $n_5$ to a value of 1, as depicted in FIG. 2. Then, the control unit 14 is configured to select for the first actuating period $T_{A1}$ a first stimulating unit 12*a* and for the second actuating period $T_{A5}$ a second stimulating unit 12*c* which are to be individually actuated during the respective actuating period $T_{A1}$, $T_{A5}$. In other words, the control unit 14 is configured to select a single first stimulating unit to be individually actuated during a first actuating period and a single second stimulating unit to be individually actuated during a second actuating period.

Further, the control unit 14 is configured to set for a third actuating period, e.g. $T_{A3}$, the number $n_3$ to a value of 2. Then, the control unit 14 is configured to select for the third actuating period $T_{A3}$ two stimulating units 12*a*, 12*c* which are to be actuated simultaneously during the third actuating period $T_{A3}$. In other words, the control unit 14 is configured to select at least two stimulating units to be actuated simultaneously during a third actuating period.

For variedly selecting the stimulating units 12*a-d* to be actuated during the sequence S, the control unit 14, for each of the actuating periods $T_{A1, \ldots, Ai}$, is configured to stochastically and/or deterministically and/or combined stochastically-deterministically select the determined number $n_{1, \ldots, i}$ of stimulating units 12*a-d* from the set of stimulating units. For example, for doing so, the control unit 14 may employ an exponential distribution process and/or a Markov process and/or any other suitable stochastic or deterministic or combined stochastic-deterministic process. In this way, regularities or periodicities in the sequence S may be avoided, thereby contributing to a robust and effective suppression of pathologically synchronous activity of the patient's neurons.

In a further development, the stimulating units 12*a-d* may be provided with an equal probability or with differing probabilities for being selected by the control unit 14. Accordingly, the control unit may select the stimulating units 12*a-d* in dependence of predefined probabilities for the individual stimulating units 12*a-d*. In this way, the frequency of occurrence of individual stimulating units 12*a-d* to being actuated may be set across the sequence S. For example, individual stimulating units 12*a-d* may be provided with a higher relative probability such that they are actuated more frequently during the sequence S.

Additionally or alternatively, the control unit 14 may be configured to select the stimulating units 12*a-d* for the respective actuating periods $T_{A1, \ldots, Ai}$ in dependence of a predefined probability or a predefined frequency of occurrence for single stimulating units 12*a-d* to be individually or exclusively actuated during the actuating periods $T_{A1, \ldots, Ai}$ in the sequence S and/or for a combination of stimulating units 12*a-d* to be simultaneously actuated during the actuating periods $T_{A1, \ldots, Ai}$ in the sequence S. For example, for a combination of two stimulating units 12*a-d*, a probability or frequency of occurrence may be set as 0 so as to avoid that these two stimulating units 12*a-d* are actuated simultaneously during the sequence S. In other words, the predefined probability or frequency of occurrence may be set so as to prevent single stimulating units 12*a-d* to be individually or exclusively actuated and/or a specific combination of stimulating units 12*a-d* to be simultaneously actuated in the sequence S. In a further example, a probability or frequency of occurrence for specific single stimulating units 12*a-d* to be individually actuated and/or for specific combinations of stimulating units 12*a-d* to be simultaneously actuated may be set relatively high such that they are actuated more frequently during the sequence S. Further, the predefined probabilities or frequencies of occurrence may vary during the course of the sequence S.

As set forth above, the stimulating units 12*a-d* can be operated in different operational modes, in which the respective stimulating units 12*a-d* generate different stimuli, i.e. in terms of stimuli duration, vibration frequency, vibration amplitude, etc. Accordingly, the control unit 14 is configured to variedly select for each of the selected stimulating units 12*a-d* one operational mode from a predefined set of operational modes for the respective stimulating unit 12*a-d*.

In the shown embodiment, as depicted in FIG. 2, each of the stimulating units 12*a-d* may be operated in a first operational mode denoted as "O1" and a second operational mode denoted as "O2", wherein the actuating modes for a respective stimulating unit 12*a-d* differ in the characteristic of the stimuli to be generated by the stimulating unit 12*a-d* in terms of, for example, stimuli duration, stimuli strength, e.g. vibratory amplitude, stimuli frequency and/or stimuli time course. In FIG. 2, the different operational modes O1 and O2 are illustrated by different hatching of the actuation fields. Specifically, for variedly selecting the operational modes, the control unit 14 is configured to stochastically and/or deterministically and/or combined stochastically-deterministically select for each of the selected stimulating units 12*a-d* one operational mode from the predefined set of operational modes for the respective stimulating unit 12*a-d*. For doing so, the control unit 14 may employ an exponential distribution process and/or a Markov process and/or any other suitable stochastic or deterministic or combined stochastic-deterministic process.

As set forth above and as depicted in FIG. 2, between successive actuating periods $T_{A1, \ldots, Ai}$, resting periods $T_{R1, \ldots, Ri}$ are scheduled. These resting periods $T_{R1, \ldots, Ri}$ are generated or stipulated by the control unit 14. Specifically, the control unit 14 is configured to variedly determine a duration of each resting period $T_{R1, \ldots, Ri}$ in the sequence S. In this context, the term "variedly" means that the determined durations of the resting periods $T_{R1, \ldots, Ri}$ diversely, i.e. non-periodically, vary across the sequence S. The control unit 14 may be configured to, for at least one resting period $T_{R1, \ldots, RI}$, set a duration to 0 s, such that two successively scheduled actuating periods $T_{A1, \ldots, Ai}$ may directly follow one after another in the sequence.

For variedly determining the resting periods $T_{R1, \ldots, Ri}$, the control unit 14 is configured to stochastically and/or deterministically and/or combined stochastically-deterministically determine the durations of the resting periods $T_{R1, \ldots, Ri}$. For example, for doing so, the control unit 14 may employ an exponential distribution process and/or a Markov process and/or any other suitable stochastic or deterministic or combined stochastic-deterministic process. In this way, regularities or periodicities in the sequence S may be avoided which may unfavorably interfere with periodicities intrinsic to the pathologically synchronous and oscillatory neuronal activity.

For easier handling, in the following, the sum of an actuating period $T_{Rx}$ and a subsequent resting period $T_{Rx}$ is referred to as an actuation cycle $T_{Cx}$. It had been found that a small amount of periodicity or repetition in the set of actuation cycles $T_{C1, \ldots, Ci}$ in the sequence will typically not impair the therapeutic effects of the proposed medical treatment device 10. For example, even if the set of determined actuation cycles $T_{C1, \ldots, Ci}$ comprises 10% of identical resting period's durations, the proposed medical treatment device 10 may still provide the intended therapeutic effects.

However, the control unit 14 may be configured to determine the durations of the rest periods $T_{R1, \ldots, Ri}$ such that the set of determined actuation cycles $T_{C1, \ldots, Ci}$ comprises less than 10%, 5% or 1% of identical durations.

Alternatively, the control unit 14 may be configured to stipulate or generate the resting periods $T_{R1, \ldots, Ri}$ such that, in the sequence S, the resting periods $T_{R1, \ldots, Ri}$ or the actuation cycles $T_{C1, \ldots, Ci}$ have an equal duration.

As set forth above, a number of brain disorders are associated with characteristic abnormal neuronal oscillatory activity in particular frequency bands. For instance, depth recordings in the basal ganglia of patients with Parkinson's disease revealed tremor-related theta band (4 Hz to 7 Hz) activity and bradykinesia-related beta band (9 Hz to 35 Hz) activity. In particular, abnormal neuronal oscillations can be found in different frequency bands.

Accordingly, the control unit 14 may be configured to determine the resting periods $T_{R1, \ldots, Ri}$ such that a mean frequency of the actuating sequence S does not exceed the upper band edge of the lowest frequency band associated with the brain disease, e.g. 7 Hz in Parkinson patients with tremor. The mean frequency may correspond to or be calculated by the inverse of the sum of a mean actuating periods' duration and a mean resting periods' duration in the sequence S. Alternatively, the control unit 14 may be configured to determine the resting periods $T_{R1, \ldots, Ri}$ such that the mean frequency of the actuating sequence S is in the range of 5% of the lowest dominant frequency associated with the brain disease or it is up to 2 times or even up to 5 times below the dominant frequency associated with the brain disease.

Figure 3:
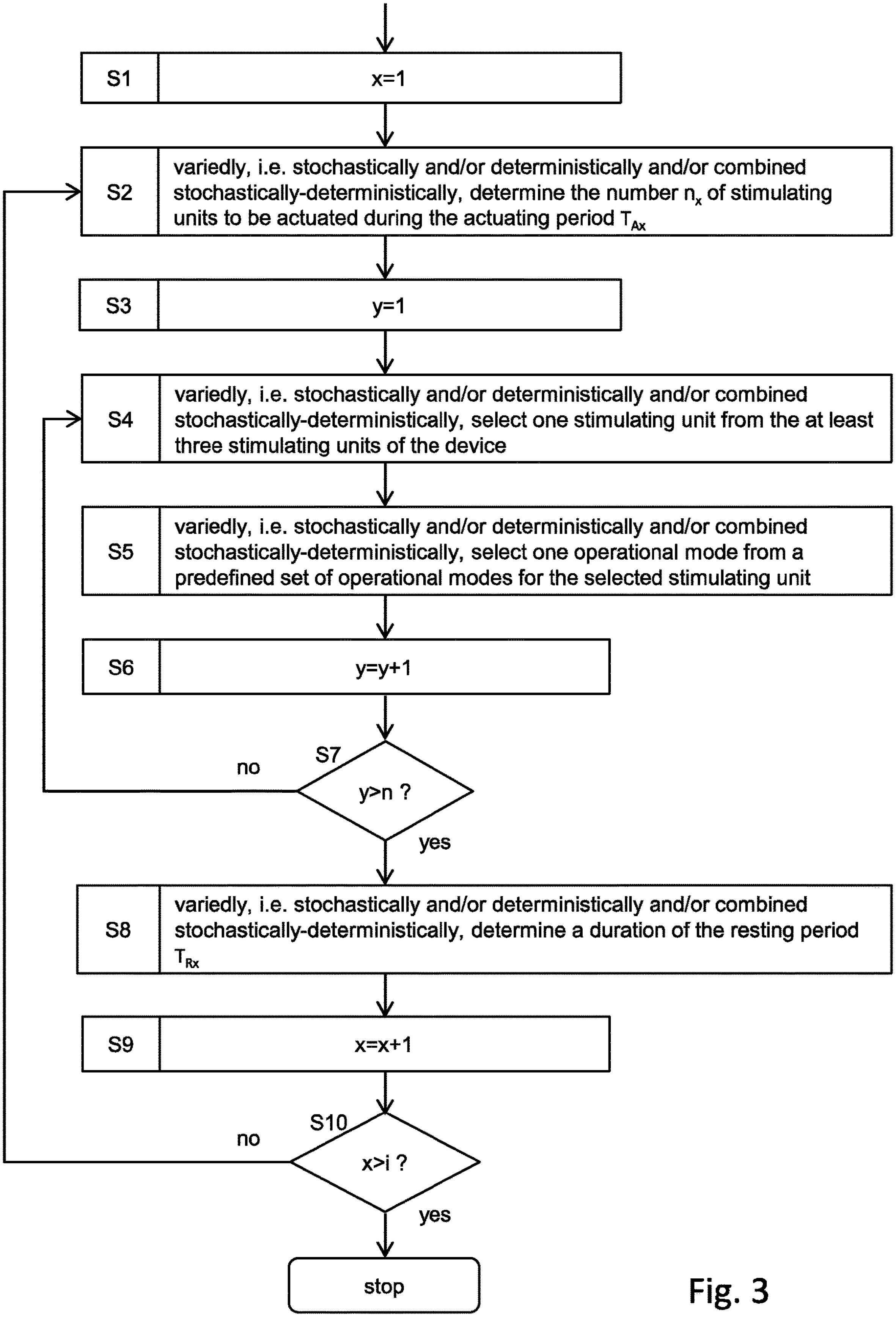
FIG. 3 shows a flow diagram illustrating a procedure employed by a control unit of the medical treatment device for generating the sequence depicted in FIG. 2.

FIG. 3 shows a flow diagram illustrating a procedure employed by the control unit 14 for generating the sequence S. The procedure may be performed by the control unit 14 prior to actuating the stimulating units 12*a-d* according to the generated sequence S. Alternatively, the procedure may be performed successively during the sequences S, i.e. during actuating the stimulating units 12*a-d*.

In the following, the steps of the procedure are described in more detail under reference of FIG. 3. The sequence S comprises the number i of different actuating periods $T_{A1, \ldots, Ai}$, as depicted in FIG. 2. In the shown procedure, steps S2 to S10 are repeatedly and successively executed for each of the actuating periods $T_{A1, \ldots, Ai}$.

In a first step S1, a value of a control variable x is set to equal 1. In this way, in the steps S2 to S7 of the procedure, initially, the first actuating period $T_{A1}$ of the sequence S is generated. Specifically, in step S2, the control unit 14 variedly, i.e. stochastically and/or deterministically and/or combined stochastically-deterministically, determines the number $n_1$ of stimulating units 12*a-d* to be actuated during the actuating period $T_{A1}$. Then, in steps S4 to S7, the control unit 14 successively selects the determined number $n_1$ of stimulating units from the four stimulating units 12*a-d* of the medical treatment device 10, wherein the steps are performed such that, for each actuating period $T_{A1, \ldots, Ai}$, each of the plurality of stimulating units 12*a-d* can only be selected once. Specifically, for each of the selected stimulating units 12*a-d*, the control unit 14 variedly, i.e. stochastically and/or deterministically and/or combined stochastically-deterministically, selects one operational mode from the predefined set of operational modes for the selected stimulating unit 12*a-d* according to step S5.

Thereafter, in step S8, the control unit 14 variedly, i.e. stochastically and/or deterministically and/or combined stochastically-deterministically, determines a duration of the resting period $T_{R1}$. Next, in step S9, the control variable x is increased by 1 and the aforementioned steps S2 to S9 are repeated until the control variable x exceeds the total number i of different actuating periods $T_{A1, \ldots, Ai}$ to be generated in the sequence S.

Figure 4:
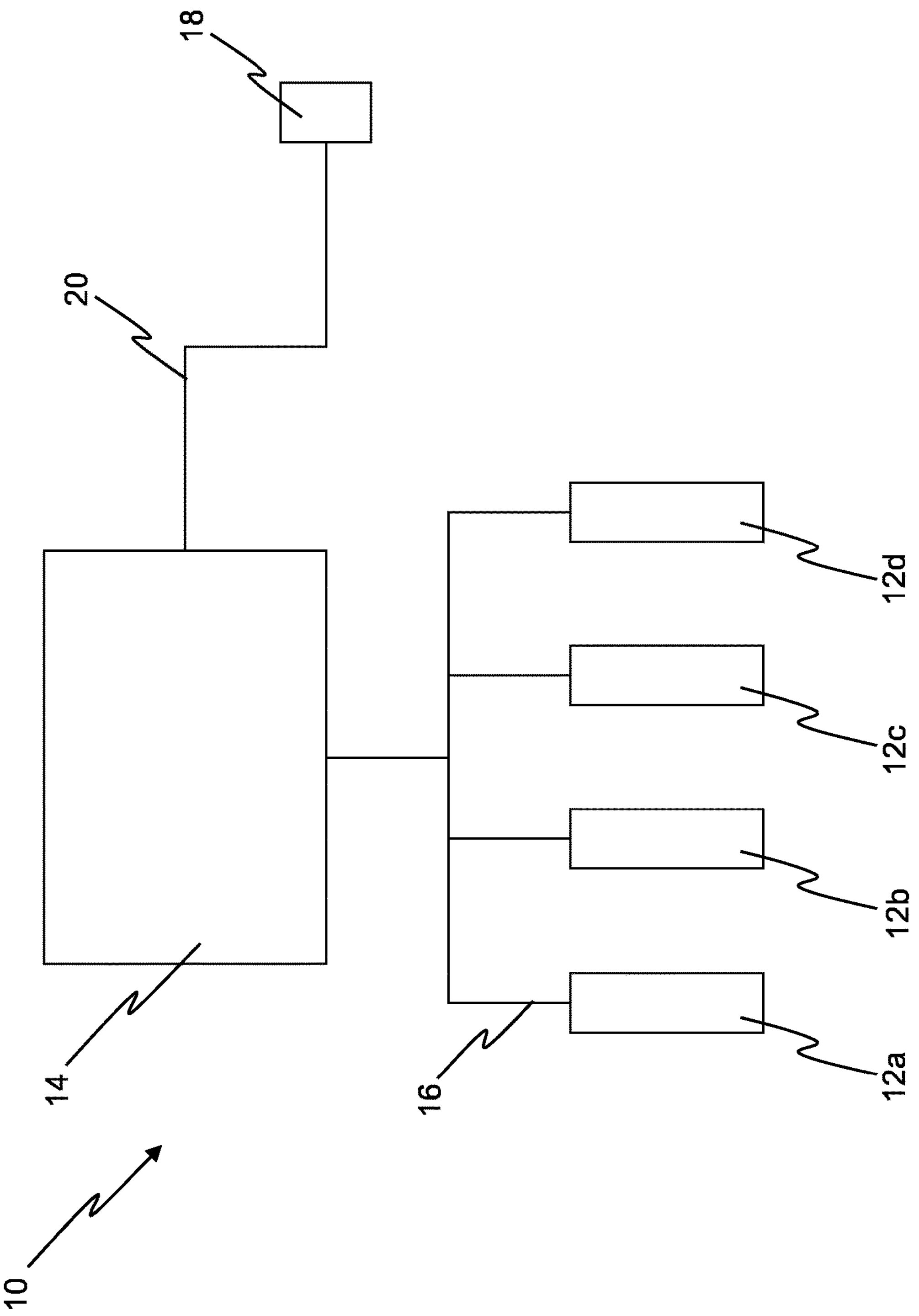
FIG. 4 is a schematic illustration of a medical treatment device according to a second embodiment.

FIG. 4 shows another embodiment of the medical treatment device 10. Compared to the embodiment depicted in FIG. 1, the medical device 10 of FIG. 4 comprises means for closed loop-control of the stimulation generated by the stimulating units 12*a-d*. Accordingly, the medical treatment device 10 further comprises a sensor unit 18 for measuring or assessing stimulation effects and/or neuronal activity, i.e. in the patient's brain or spinal cord, and/or muscular activity. Thus, the medical treatment device 10 comprises a further fastening means for coupling the sensor unit 18 to the patient's body. The sensor unit 18 is connected to the control unit 14 via a connecting via 20, through which it guides measured or assessed information or data to the control unit 14. Alternatively, the sensor 18 may be wirelessly connected to the control unit 14.

In this configuration, the control unit 14 is configured to generate or adapt the sequence S of successive actuating periods $T_{A1, \ldots, Ai}$ in dependence on the information acquired by the sensor unit 18. Specifically, the control unit 14 is configured to, in dependence on the information acquired by the sensor 18, determine the number $n_{1, \ldots, i}$, select the determined number $n_{1, \ldots, i}$ of different stimulating units 12*a-d* for each actuating period $T_{A1, \ldots, Ai}$, select for each selected stimulating unit 12*a-d* an operational mode, and/or determine a duration of each resting period $T_{R1, \ldots, Ri}$.

The sensor unit 18 may comprise at least one non-invasive sensor. For example, it may comprise sensors for acquiring Electroencephalography (EEG) recordings (assessing brain activity), Magnetoencephalography (MEG) recordings (assessing brain activity), Electromyography (EMG) recordings (assessing muscular activity, e.g. tremor). Further, the sensor unit may comprise sensors for registering kinematic parameters, such as accelerometers (to measure tremor or amount of movement production).

Alternatively or additionally, the sensor unit 18 may comprise at least one invasive sensor. For example, such an invasive sensor may be provided in the form of electrodes, e.g. epicortical, epidural, intracortical or depth electrodes, configured to be implanted in the patient's brain, in order to provide signals, in particular local field potentials (LFP), generated by active neurons. A less invasive alternative are subcutaneous electrodes, i.e. electrode implanted under the skin of the head.

More specifically, in one embodiment, the control unit 14 may be configured to adapt characteristics of the stimuli generated by the stimulating units 12*a-d*, e.g. in terms of stimuli duration, stimuli strength, stimuli frequency and/or stimuli time course, in dependence of the information or data acquired by the sensor unit 18. For example, in case the sensor unit 18 detects or measures increased levels of disease-related spectral power in EEG, MEG, EMG or LFP recordings, the control unit 14 may be configured to respectively increase stimulation intensity by increasing amplitude of and/or duration of single stimuli generated by the stimulating units 12*a-d*.

In a further development, the control unit 14 may be configured to iteratively adapt the characteristics of the stimuli generated by the stimulating units 12*a-d* in dependence of the information or data acquired by the sensor unit 18. In particular, the control unit 14 may be configured to analyze the acquired data of the sensor unit 18 so as to selectively adapt the characteristics of the stimuli generated by the stimulating units 12*a-d*. For example, the control unit 14 may perform a spectral analysis based on EEG, MEG, EMG and/or LFP recordings acquired by the sensor unit 18. Then, over the duration of one or more treatment procedures performed by the medical treatment device 10, the control unit 14 may be configured to register changes of brain activity, in particular, changes of spectral power in disease-related frequency bands (e.g. theta and/or beta band in Parkinson's disease) caused by stimulating the patient's body by means of the stimulating units 12*a-d*. Thereafter, characteristics of the stimuli generated by the stimulating units 12*a-d* are stepwise or iteratively changed so as to cause changes of the spectral power and to track the changes by means of the sensor unit 18. For example, at least one of the following parameters or characteristics may be changed: vibration amplitude or amplitude of electrical pulse, length of single vibratory or electrical stimuli, number of stimulus devices, location of stimulating units 12*a-d* at the patient's body, inducing unilateral or bilateral stimulation. In this way, the control unit 14 may automatically identify and adapt relevant characteristics or parameters of the stimuli which cause most pronounced reduction of disease related spectral power.

Further, the information or data acquired by the sensor unit 18 may be used by the control unit 14 to adapt the mean frequency of the actuating sequence, i.e. by respectively changing the resting periods $T_{R1, \ldots, Ri}$ in the sequence S. For example, the control unit 14 may perform a spectral analysis based on EEG, MEG, EMG and/or LFP recordings acquired by the sensor unit 18 so as to determine dominant oscillatory frequency components. Based thereupon, the control unit 14 may be configured to adapt the mean frequency of the actuating sequence S such that it is in the range of ±5% of the lower bound of the lowest dominant frequency of the feedback signal, or it is at the lower edge of the lowest dominant frequency of the feedback signal, or it is up to 2 times or even up to 5 times below the dominant frequency of the feedback signal.

Additionally or alternatively, the control unit 14 may be configured to, in response to the acquired data or information by the sensor unit 18, generate a warning signal for the patient, the warning signal being indicative of, for example, increasing a daily treatment duration. Accordingly, the medical treatment device 10 may comprise a means for outputting the warning signal, e.g. a display or a transmitting unit. Specifically, the transmitting unit may be configured to output the warning signal to a mobile device, such as a mobile phone, of the patient capable of displaying the warning signal to the patient.

Figure 5:
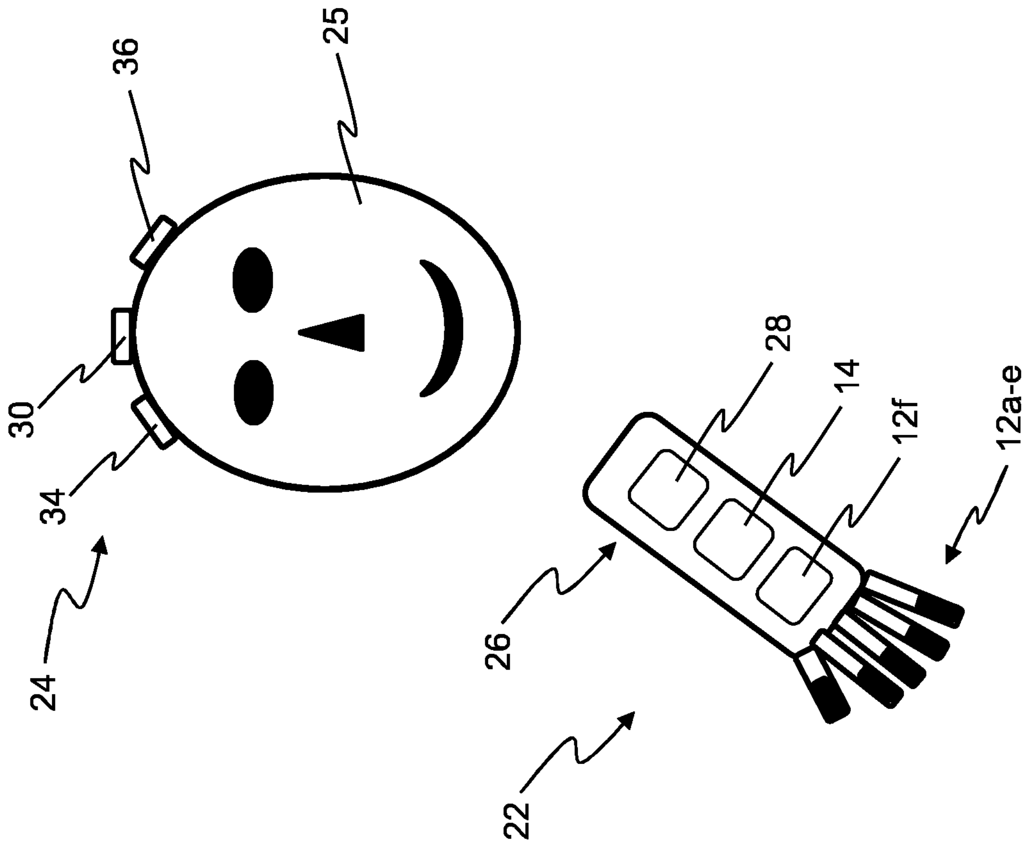
FIG. 5 is a schematic illustration of a medical treatment device in the form of a medical treatment glove.

FIG. 5 schematically shows a medical treatment device in the form of a medical treatment glove 22 for stimulating neurons of a patient to suppress a pathologically synchronous activity which may wirelessly be coupled to a sensor unit 24. The medical treatment glove 22 is fastened to a patient's right hand 26 and the sensor unit 24 may be fastened to a patient's head 25. In this configuration, the sensor unit 24 is optional.

The medical treatment glove 22 forms a medical treatment device 10 as previously described. Thus, technical features that are described above in connection with the medical treatment device 10 may also relate and be applied to the medical treatment glove 22.

The medical treatment glove 22 comprises five first stimulating units 12*a-e* fastened to different fingers, i.e. fingertips, of the patient's hand 26 and at least one second stimulating unit 12*f* fastened to a back of the patient's hand. The stimulating units 12*a-f* may comprise qualitatively different mechanical stimulators. For example, the first stimulating units 12*a-e* may comprise piezo vibrators and the second stimulating unit 12*f* may comprise a linear motor or a voice coil.

Further, the medical treatment glove 22 comprises a control unit 14 for selectively and intermittently actuating the stimulating units 12*a-f* in a sequence of actuating periods, wherein the control unit 14, across the sequence of actuating periods, is configured to variedly determine for each actuating period a number n of stimulating units to be simultaneously actuated during the respective actuating period. The control unit 14 may be configured to prevent that two first stimulating units 12*a-e* fastened to two neighboring fingers and/or all first stimulating units 12*a-e* are simultaneously actuated during the sequence.

The medical treatment glove 22 further comprises a wireless communication unit 28 connected to the control unit 14 and configured to enable a communication between the control unit 14 and the sensor unit 24. A rechargeable battery (not shown) is provided for supplying electrical energy to each one of the stimulating units 12*a-f*, the control unit 14 and the wireless communication unit 28. Further, the stimulating units 12*a-f*, the control unit 14, the wireless communication unit 28 and the rechargeable battery are embedded in the medical treatment glove 22 by means of releasable Velcro fixations means.

The sensor unit 24 is configured for measuring stimulation effects on and a neuronal activity of neurons in the patient's head 25. For transmitting the thus acquired information or data to the control unit 14, the sensor unit 24 comprises a further communication unit 30 for wirelessly communicating with the communication unit 28 of the medical treatment glove 22.

More specifically, for measuring stimulation effects and neuronal activities, the sensor unit 24 comprises two non-invasive EEG electrodes 34 connected to a controller 36 of the sensor unit 24. In an alternative embodiment, the sensor unit 24 may alternatively or additionally comprise invasive electrodes (not shown), e.g. epicortical electrodes, implanted or configured to being implanted in the patient's head 25 and connected to the controller 36.

The controller 36 amplifies and analyzes the signals provided by the electrodes 34 and wirelessly transmits the thus acquired information to the control unit 14 of the medical treatment glove 22 via the communication units 28, 30. In an alternative embodiment, the control unit 14 of the medical treatment glove 22 may be connected to the controller 36 of the sensor unit 36 via a connecting wire.

In a further development, a further medical treatment glove for the patient's left hand may be additionally provided. The further medical treatment glove may comprise, similar to the configuration of the medical treatment glove 22 for the patient's right hand, five first stimulating units fastened to different fingers, i.e. fingertips, of the patient's left hand and at least one second stimulating unit fastened to a back of the patient's left hand. Further it may respectively comprise a control unit connected to the stimulating units and to a wireless communication unit for wirelessly coupling the control unit of the left medical treatment glove with the control unit 14 of the right medical treatment glove 22. Specifically, the control unit 14 of the right medical treatment glove 22 may function as a central control unit for generating control signals for actuating the stimulating units of both the right and the left medical treatment glove according to a sequence of actuating periods. Accordingly, the control unit of the left medical treatment glove may be configured to receive the control signals from the control unit 14 of the right medical treatment glove 22, according to which it actuates the respective stimulating units. In this configuration, the left and the right hand medical treatment glove together with the sensor unit form a medical treatment system for stimulating neurons of a patient to suppress a pathologically synchronous activity thereof. The medical treatment system may comprise further and/or other medical treatment devices, the operation of which may be controlled by a central control unit associated to a control unit of one of the medical treatment devices or associated to a central control unit, e.g. a personal computer, provided separately from the medical treatment devices.

Figure 6:
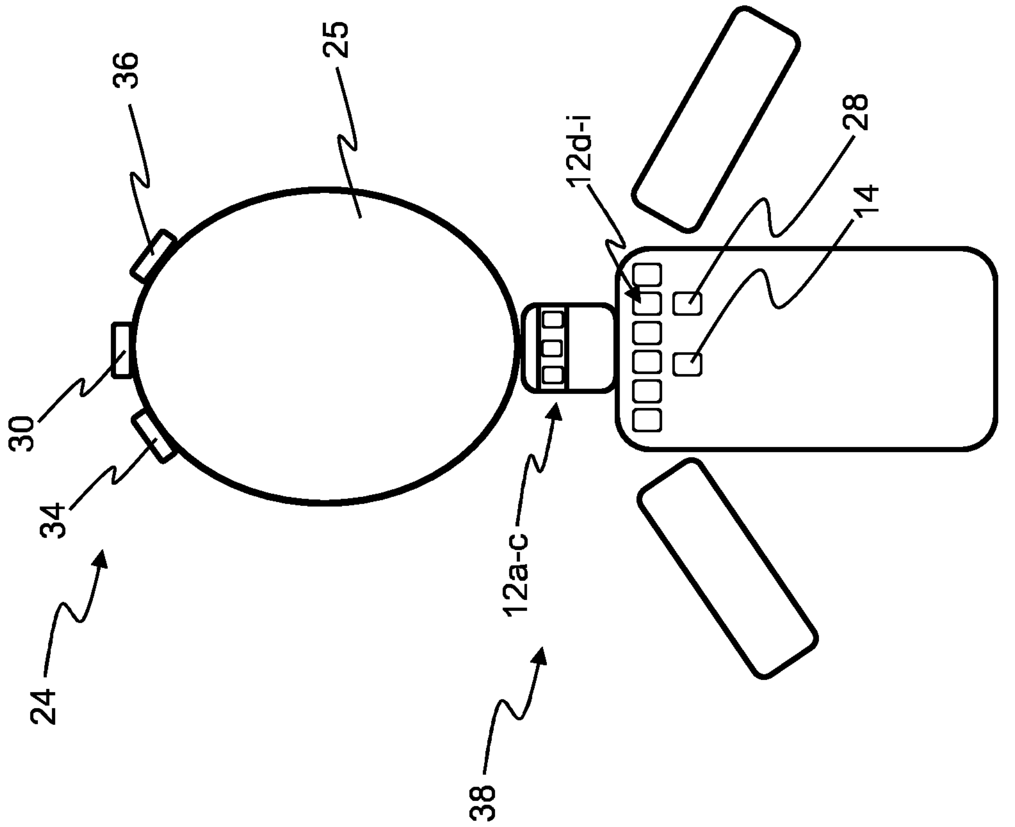
FIG. 6 is a schematic illustration of a medical treatment device in the form of a medical treatment neck and/or shoulder band.

FIG. 6 schematically shows a medical treatment device in the form of a medical treatment neck and/or shoulder band 38 for stimulating neurons of a patient to suppress a pathologically synchronous activity which may be wirelessly coupled to a sensor unit 24. The medical treatment neck and/or shoulder band 38 is fastened to a patient's neck and/or shoulder and the sensor unit 24 may be fastened to a patient's head 25. In this configuration, the sensor unit 24 is optional.

The medical treatment neck and/or shoulder band 38 forms a medical treatment device 10 as described above. Thus, technical features that are previously described in connection with the medical treatment device 10 and/or the medical treatment glove 22 may also relate and be applied to the medical treatment neck and/or shoulder band 38.

The medical treatment neck and/or shoulder band 38 comprises a plurality of first stimulating units 12*a-c* fastened to a patient's neck and/or a plurality of second stimulating units 12*d-i* fastened to a patient's shoulder. The first and second stimulating units may be configured to generate vibratory stimuli with a vibration frequency between 10 Hz and 300 Hz, i.e. between 70 Hz and 120 Hz, and a peak-to-peak vibration amplitude up to 0.8 mm.

Figure 7:
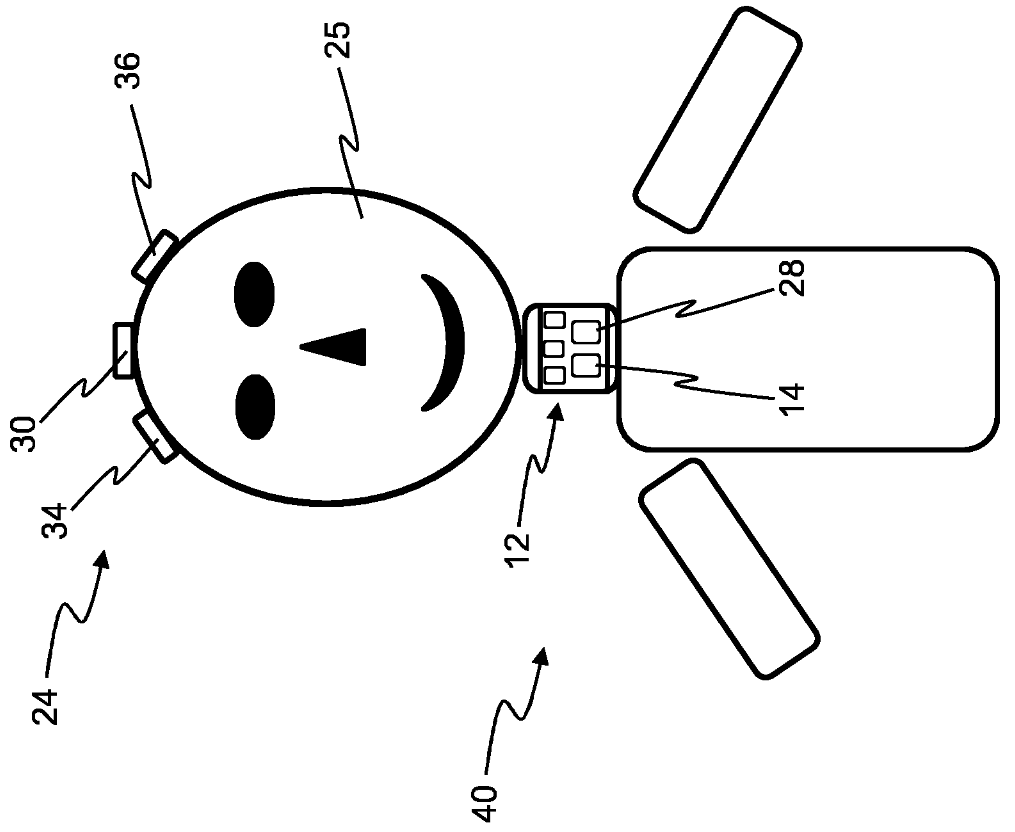
FIG. 7 is a schematic illustration of a medical treatment device in the form of a medical treatment voice box band.

FIG. 7 schematically shows a medical treatment device in the form of a medical treatment voice box band 40 for stimulating neurons of a patient to suppress a pathologically synchronous activity which may be wirelessly coupled to a sensor unit 24. The medical treatment voice box band 40 is fastened to a patient's neck by means of a neck band or neck cuff and the sensor unit 24 may be fastened to a patient's head 25. In this configuration, the sensor unit 24 is optional. The medical treatment voice box band 40 forms a medical treatment device 10 as described above. Thus, technical features that are previously described may also relate and be applied to the medical treatment voice box band 40. The medical treatment voice box band 40 comprises a plurality of stimulating units located in the area of a patient's voice box.

Figure 8:
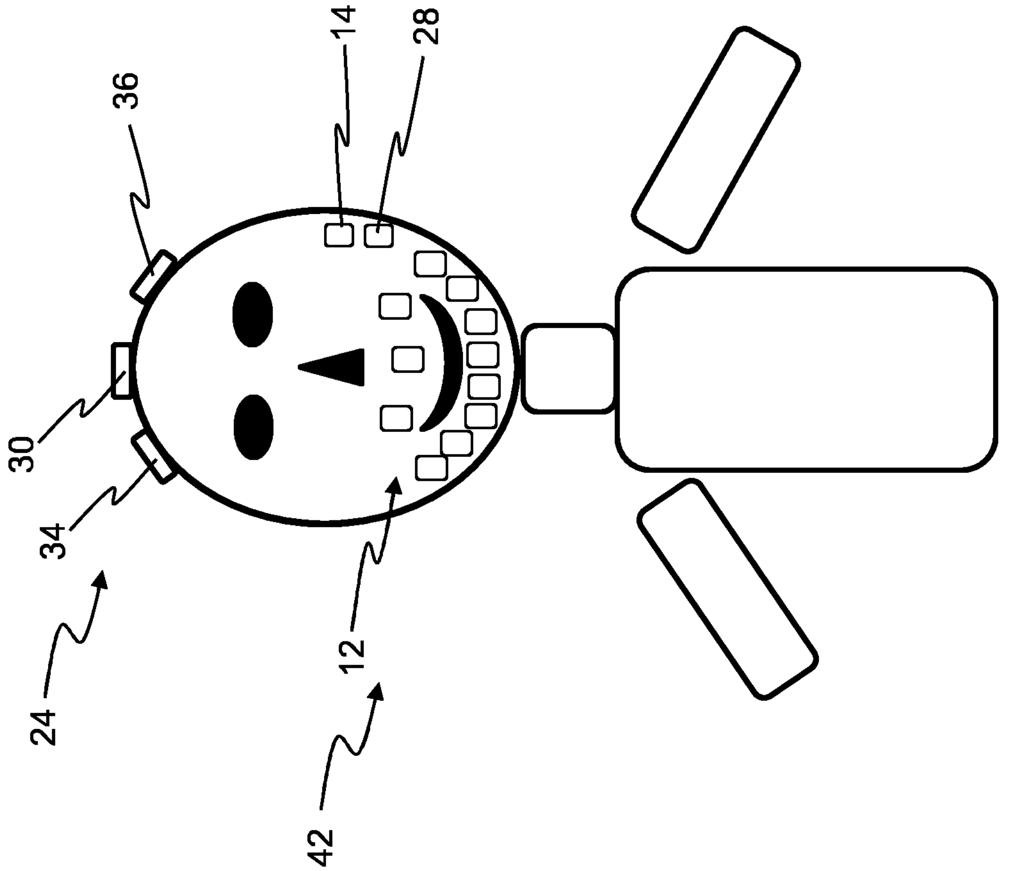
FIG. 8 is a schematic illustration of a medical treatment device in the form of a medical treatment face mask or band.

FIG. 8 schematically shows a medical treatment device in the form of a medical treatment face mask or band 42 for stimulating neurons of a patient to suppress a pathologically synchronous activity which may be wirelessly coupled to a sensor unit 24. The medical treatment face mask or band 42 is fastened to a patient's face by means of a band or a mask and the sensor unit 24 may be fastened to a patient's head 25. In this configuration, the sensor unit 24 is optional. The medical treatment face mask or band 42 forms a medical treatment device 10 as described above. Thus, technical features that are previously described may also relate and be applied to the medical treatment face mask or band 42. The medical treatment face mask or band 42 comprises a plurality of stimulating units 12 located at the facial skin of the patient.

Figure 9:
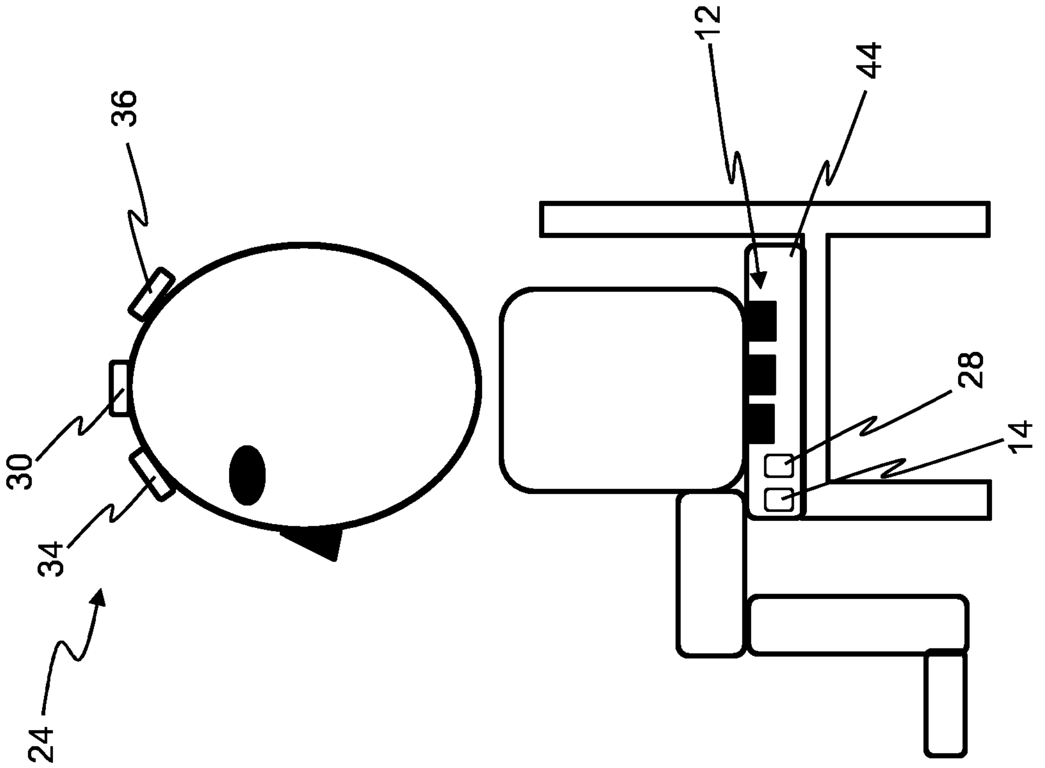
FIG. 9 is a schematic illustration of a medical treatment device in the form of a medical treatment seat pad.

FIG. 9 schematically shows a medical treatment device in the form of a medical treatment seat pad 44 for stimulating neurons of a patient to suppress a pathologically synchronous activity which may be wirelessly coupled to a sensor unit 24. The medical treatment seat pad 44 is provided and configured such that the patient can take seat on it. The sensor unit 24 may be fastened to a patient's head 25. In this configuration, the sensor unit 24 is optional. The medical treatment seat pad 44 forms a medical treatment device 10 as described above. Thus, technical features that are previously described may also relate and be applied thereto. The medical treatment seat pad 44 comprises a plurality of stimulating units 12 located in the medical treatment seat pad 44.

Figure 10:
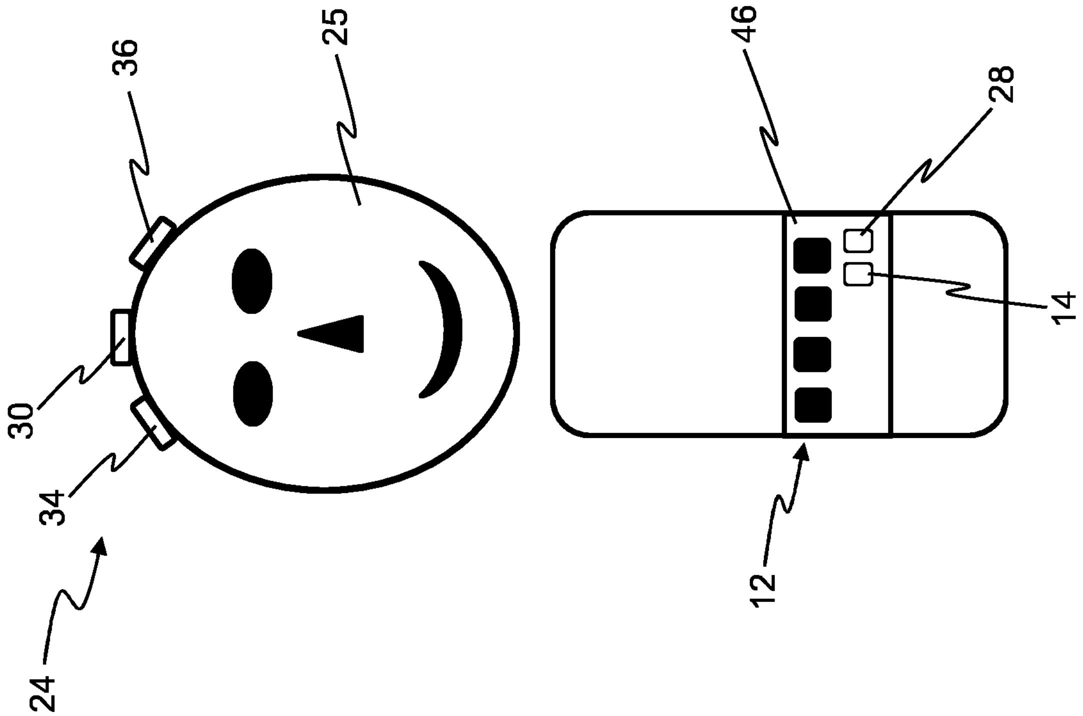
FIG. 10 is a schematic illustration of a medical treatment device in the form of a medical treatment belly band.

FIG. 10 schematically shows a medical treatment device in the form of a medical treatment belly band 46 for stimulating neurons of a patient to suppress a pathologically synchronous activity which may be wirelessly coupled to a sensor unit 24. The medical treatment belly band 46 is fastened to the patient's body in the area of a belly and the sensor unit 24 may be fastened to a patient's head 25. In this configuration, the sensor unit 24 is optional. The medical treatment belly band 46 forms a medical treatment device 10 as described above. Thus, technical features that are previously described may also relate and be applied thereto. The medical treatment belly band 46 comprises a plurality of stimulating units 12*a-h* located in the area of the patient's belly.

It will be obvious for a person skilled in the art that these embodiments and items only depict examples of a plurality of possibilities. Hence, the embodiments shown here should not be understood to form a limitation of these features and configurations. Any possible combination and configuration of the described features can be chosen according to the scope of the invention.

This is in particular the case with respect to the following optional features which may be combined with some or all embodiments, items and/or features mentioned before in any technically feasible combination.

A medical treatment device for stimulating neurons of a patient to suppress a pathologically synchronous activity may be suggested. The medical treatment device may comprise at least three non-invasive stimulating units for generating stimuli to a patient's body. The medical treatment device may further comprise a control unit for selectively and intermittently actuating the stimulating units in a sequence of actuating periods, wherein the control unit, across the sequence of actuating periods, may be configured to variedly determine for each actuating period a number n of stimulating units to be simultaneously actuated during the respective actuating period.

As set forth above, an abnormally strong synchronous activity of neurons, which induces several brain diseases, i.e. Parkinson's diseases, may be caused by abnormally upregulated synaptic connections. To counteract abnormal neuronal synchronization processes in a long-lasting, sustained manner, it is particularly favorable to downregulate the synaptic weights.

It has been found that effective down-regulation of abnormal synaptic weights can be achieved by activation of neuronal populations by mutually time-shifted activations of neuronal populations of varying composition, i.e. in terms of location and quantity. Accordingly, by providing the control unit for variedly determining the number n of stimulating units to be simultaneously actuated in the sequence of successive actuating periods, the proposed device ensures an improved and increased variability of stimulus-induced neuronal activations. As a result, neuronal populations stimulated by the stimulating units vary in terms of both location and quantity from one actuating period to another. Thereby, the device enables to effectively suppress pathologically synchronous activity of the neurons, i.e. by desynchronizing the pathologically synchronous activity of the neurons.

To that end, in known non-invasive multichannel stimulation treatment devices a plurality of different stimuli are generated according to a predefined periodical stimulation pattern which is frequently repeated, i.e. in a continuous loop, during a treatment procedure. It has been further found that such a periodical stimulation pattern may cause an activation of neurons induced by the generated stimuli which coincidently and repeatedly overlap with the pathologically synchronous activity during a treatment procedure. By contrast, the proposed medical treatment device provides time-shifted activations of neuronal populations of variedly varying composition. In this way, it may be avoided that specific neuronal populations are stimulated in a periodical manner. Thus, compared to known non-invasive multichannel stimulation treatment devices, the proposed medical treatment device is robust with respect to a detuning between a rate of stimulus delivery and dominant frequencies of pathological neuron oscillations. This is particularly favorable when the medical treatment device is operated in a non-invasive manner, i.e. without feedback from implanted invasive sensors, such as epicortical electrodes.

In a further development, for at least one of the actuating periods of the sequence, the control unit may be configured to determine at least three stimulating units to be simultaneously actuated. In other words, for at least one of the actuating periods of the sequence, the control unit sets the value of n to 3. Alternatively or additionally, the control unit may be configured to, for at least one of the actuating periods of the sequence, determine or set the value of n to 1 such that, during the respective actuating period, a single stimulating unit is individually or exclusively actuated. Alternatively or additionally, the control unit may be configured to, for at least one of the actuating periods of the sequence, determine or set the value of n to 2 such that, during the respective actuating period, two stimulating units are simultaneously actuated. In this way, a high variability of the actuating sequence can be ensured causing the neurons of the patient to fire or burst in an uncorrelated manner, thereby enabling a pronounced and robust reduction of the abnormally up-regulated synaptic weights in the target neuronal population of the patient.

The stimulating units may be configured to generate stimuli to different sites of the patient's body. In this way, a greater neuronal population may be stimulated by the medical treatment device, thereby enabling to increase a spatial variability of stimulated neurons. Specifically, the stimulating units may be configured to generate stimuli at a body surface of the patient. Alternatively or additionally, the stimulating units may be configured to generate tactile stimuli and/or vibratory stimuli and/or electrical stimuli.

The control unit may be configured to determine for the value of the number n an integer between 1 and a total number of stimulating units comprised in the medical treatment device. Alternatively, when the device comprises a number u of stimulating units that is greater than 3, the value of the number n may be an integer between 1 and u−1.

For variedly determining the number n, the control unit, for each of the actuating periods, may be configured to stochastically and/or deterministically and/or combined stochastically-deterministically determine the number n of stimulation units to be actuated simultaneously during the respective actuating periods.

Further, the control unit, across the sequence of actuating periods, is configured to variedly select the determined number n of different stimulating units from the at least three stimulating units of the device. For example, the control unit may be configured to select a single first stimulating unit to be individually actuated during a first actuating period and a single second stimulating unit to be individually actuated during a second actuating period. Further, the control unit may be configured to select at least two stimulating units to be actuated simultaneously during a third actuating period. Specifically, the control unit may be configured to, for each of the actuating periods, stochastically and/or deterministically and/or combined stochastically-deterministically select the determined number n of stimulating units from the at least three stimulating units of the medical treatment device.

Alternatively or additionally, the control unit may be configured to select the stimulating units for the respective actuating periods in dependence of a predefined probability or a predefined frequency of occurrence for single stimulating units to be individually actuated during the actuating periods in the sequence and/or for a combination of stimulating units to be simultaneously actuated during the actuating periods in the sequence. For example, the probability or predefined frequency of occurrence may be set so as to prevent single stimulating units to be individually actuated in the sequence and/or a specific combination of stimulating units to be simultaneously actuated in the sequence.

Alternatively or additionally, the control unit may be configured to variedly select for each of the selected stimulating units one operational mode from a predefined set of operational modes for the respective stimulating unit. The actuating modes, for a respective stimulating unit, may differ in the characteristic of the stimuli to be generated by the stimulating unit in terms of stimuli duration, stimuli strength, stimuli frequency and/or stimuli time course.

For example, the stimuli to be generated may be specified based on an amplitude curve which refers to a time course of stimuli strength. In this context, the stimuli may be generated with different waveforms, e.g. when being provided in the form of mechanical stimuli or vibrations. In particular, the control unit may be configured to variedly set a waveform of the different stimuli among the sequence of actuating periods and/or among the respective actuating periods. For example, for doing so, the control unit may employ an exponential distribution process and/or a Markov process and/or any other suitable stochastic or deterministic or combined stochastic-deterministic process. Specifically, the stimuli may be generated so as to be provided in the form of sine waves or trapezoidal waves.

It has been recognized that, since the different waveforms may have different power spectra, different waveforms may activate proprioceptive receptors differently. As to substance, the spectrum of a trapezoidal waveform may contain higher frequency components. Accordingly, given the known tuning characteristics of the above described RA (rapidly adapting) units and the above described PC (Pacinian corpuscles) units, a 30 Hz vibration with a sine wave at sufficiently small vibration amplitude may activate, i.e. predominantly activate, receptors of the RA units, also referred to as the fast-adapting type I (FA I) units. Further, a 30 Hz vibration with a trapezoidal waveform having substantially corresponding or identical vibration amplitudes compared to the sine wave may additionally activate receptors of the PA units, also referred to as the fast-adapting type II (FA II) units.

Accordingly, to vary the extent and composition of the neuronal subpopulations stimulated by the different vibratory stimuli delivered to the same part of the body, e.g. to the same fingertip, the stimulus waveform, in particular within a sequence, may be varied, e.g. from one stimulus to another and in particular in a deterministic or stochastic or combined deterministic-stochastic manner.

In a further development, the control unit may be configured to stipulate resting periods between successive actuating periods. Accordingly, the control unit may be configured to variedly determine a duration of each resting period across the sequence. In this way, a higher variability of the actuating sequence can be ensured causing the neurons of the patient to fire or burst in an uncorrelated manner, thereby enabling a pronounced and robust reduction of the abnormally up-regulated synaptic weights in the target neuronal population of the patient. Specifically, the control unit may be configured to stochastically and/or deterministically and/or combined stochastically-deterministically determine the duration of each of the resting periods.

The medical treatment device may further comprise a sensor unit for measuring stimulation effects on the neurons, wherein the control unit may be configured to adapt the stimuli generated by the stimulating units and/or the sequence of actuation periods in dependence on the information measured by the sensor unit.

Further, a medical treatment glove for being fastened to a patient's hand and for stimulating neurons of the patient to suppress a pathologically synchronous activity may be proposed. The medical treatment glove may form or comprise a medical treatment device as described above. Thus, technical features that described in connection with the medical treatment device may also relate and be applied to the medical treatment glove.

Further, a medical treatment band for being fastened to a patient's body and for stimulating neurons of the patient to suppress a pathologically synchronous activity may be proposed. The medical treatment band may form or comprise a medical treatment device as described above. Thus, technical features described in connection with the medical treatment device may also relate and be applied to the medical treatment band. Specifically, the medical treatment band may be a medical treatment neck and/or shoulder band, a medical treatment voice box band, a medical treatment face band and/or a medical treatment belly band.

In addition, a medical treatment seat pad for stimulating neurons of the patient to suppress a pathologically synchronous activity is proposed, on which a patient can take seat. The medical treatment seat pad may form or comprise a medical treatment device as described above. Thus, technical features described in connection with the medical treatment device may also relate and be applied thereto.

Further, a medical treatment sole, i.e. an insole, for stimulating neurons of the patient to suppress a pathologically synchronous activity is provided. The medical treatment sole may form or comprise a medical treatment device as described above. Thus, technical features described in connection with the medical treatment device may also relate and be applied thereto.

In addition, a medical treatment system for stimulating neurons of a patient to suppress a pathologically synchronous activity may be proposed, the medical treatment system comprising two or more above described medical treatment devices. Specifically, the medical treatment system may further comprise a central control unit for generating control signals for the medical treatment devices. For example, the central control unit may be constituted by a control unit of one of the medical treatment devices.

Still further, a medical treatment method for stimulating neurons of a patient to suppress a pathologically synchronous activity is proposed. The method may comprise the steps of providing at least three non-invasive stimulating units for generating stimuli to a patient's body, and of selectively and intermittently actuating the stimulating units according to a sequence of actuating periods, wherein a number n of stimulating units to be simultaneously actuated during the respective actuating period may variedly vary across the sequence, and wherein, during at least one of the actuating periods, three stimulating units may be simultaneously actuated. Alternatively or additionally, during at least one of the actuating periods, a single stimulating unit may be exclusively or individually actuated. Alternatively or additionally, during at least one of the actuating periods, exclusively two stimulating units may be simultaneously actuated. The proposed method may be employed in a medical treatment device as described above. Thus, technical features described in connection with the medical treatment device may also relate and be applied thereto.

The invention claimed is:

1. A medical treatment device for stimulating neurons of a patient to suppress a pathologically synchronous activity, the device comprises:

at least three non-invasive stimulating units for generating stimuli to a patient's body, and a control unit for selectively and intermittently actuating the stimulating units in a sequence of actuating periods, wherein the control unit, across the sequence of actuating periods, is configured to variedly and non-periodically determine for each actuating period a number n of stimulating units to be simultaneously actuated during the respective actuating period, wherein n is an integer equal to or greater than one.

2. The medical treatment device according to claim 1, wherein, for at least one of the actuating periods of the sequence, the control unit is configured to determine at least three stimulating units to be simultaneously actuated.

3. The medical treatment device according to claim 1, wherein the stimulating units are configured to generate stimuli to different sites of the patient's body.

4. The medical treatment device according to claim 1, wherein the stimulating units are configured to generate stimuli at a body surface of the patient.

5. The medical treatment device according to claim 1, wherein the stimulating units are configured to generate tactile stimuli and/or vibratory stimuli and/or electrical stimuli.

6. The medical treatment device according to claim 1, wherein n is an integer between 1 and a total number of stimulating units comprised in the medical treatment device.

7. The medical treatment device according to claim 1, wherein, when the device comprises a number u of stimulating units that is greater than 3, the number n is an integer between 1 and u−1.

8. The medical treatment device according to claim 1, wherein the control unit, for each of the actuating periods, is configured to stochastically and/or deterministically and/or combined stochastically-deterministically determine the number n of stimulation units to be actuated simultaneously during the respective actuating periods.

9. The medical treatment device according to claim 1, wherein the control unit, across the sequence of actuating periods, is configured to variedly select the determined number n of different stimulating units from the at least three stimulating units of the device.

10. The medical treatment device according to claim 1, wherein the control unit is configured to select a single first stimulating unit to be individually actuated during a first actuating period and a single second stimulating unit to be individually actuated during a second actuating period.

11. The medical treatment device according to claim 10, wherein the control unit is configured to select at least two stimulating units to be actuated simultaneously during a third actuating period.

12. The medical treatment device according to claim 1, wherein, for each of the actuating periods, the control unit is configured to stochastically and/or deterministically and/or combined stochastically-deterministically select the determined number n of stimulating units from the at least three stimulating units of the medical treatment device.

13. The medical treatment device according to claim 1, wherein the control unit is configured to select the number n of stimulating units for the respective actuating periods based at least in part on:

a predefined probability or a predefined frequency of occurrence assigned to single stimulating units to be individually actuated during the actuating periods in the sequence and/or, a predefined probability or a predefined frequency of occurrence assigned to a combination of stimulating units to be simultaneously actuated during the actuating periods in the sequence.

14. The medical treatment device according to claim 13, wherein the predefined frequency of occurrence is set so as to prevent single stimulating units to be individually actuated in the sequence and/or a specific combination of stimulating units to be simultaneously actuated in the sequence.

15. The medical treatment device according to claim 1, wherein the control unit is configured to variedly select for each of the selected stimulating units one operational mode from a predefined set of operational modes for the respective stimulating unit.

16. The medical treatment device according to claim 15, wherein the operational modes for a respective stimulating unit differ in the characteristic of the stimuli to be generated by the stimulating unit in terms of stimuli duration, stimuli strength, stimuli frequency and/or stimuli time course.

17. The medical treatment device according to claim 1, wherein the control unit is configured to stipulate resting periods between successive actuating periods.

18. The medical treatment device according to claim 17, wherein the control unit is configured to variedly determine a duration of each resting period across the sequence.

19. The medical treatment device according to claim 18, wherein the control unit is configured to stochastically and/or deterministically and/or combined stochastically-deterministically determine the duration of each of the resting periods.

20. The medical treatment device according to claim 1, further comprising a sensor unit for measuring stimulation effects on the neurons, wherein the control unit is configured to adapt the stimuli generated by the stimulating units and/or the sequence of actuation periods in dependence on the information measured by the sensor unit.

* * * * *